United States Patent

Flanagan et al.

[11] Patent Number: 5,231,093
[45] Date of Patent: Jul. 27, 1993

[54] CARBAMATE DERIVATIVES OF 4-AMINO-3-ISOXAZOLIDINONES, 3-AMINO-1-HYDROXYPYRROLIDIN-2-ONES AND 1-AMINO-1-CYCLOPROPANECARBOXYLIC ACID ANALOGS

[75] Inventors: Denise M. Flanagan, Bridgewater; Lawrence L. Martin, Lebanon, both of N.J.

[73] Assignee: Hoechst-Roussel Pharmaceuticals Incorporated, Somerville, N.J.

[21] Appl. No.: 924,999

[22] Filed: Aug. 5, 1992

Related U.S. Application Data

[62] Division of Ser. No. 769,268, Oct. 1, 1991, Pat. No. 5,153,193.

[51] Int. Cl.$^5$ .................. A61K 31/55; C07D 491/107
[52] U.S. Cl. ........................... 514/215; 540/581
[58] Field of Search ...................... 540/581; 514/215

[56] References Cited

U.S. PATENT DOCUMENTS 5,153,193 10/1992 Flanagan ........................... 514/215

Primary Examiner—Robert T. Bond
Attorney, Agent, or Firm—Tatsuya Ikeda

[57] ABSTRACT

There are disclosed various compounds of the formula below,

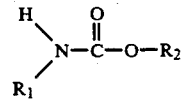

where the parameters $R_1$ and $R_2$ are as defined in the specification, which compounds are useful for alleviating various memory dysfunctions characterized by a cholinergic deficit such as Alzheimer's disease.

14 Claims, No Drawings

CARBAMATE DERIVATIVES OF 4-AMINO-3-ISOXAZOLIDINONES, 3-AMINO-1-HYDROXYPYRROLIDIN-2-ONES AND 1-AMINO-1-CYCLOPROPANECARBOXYLIC ACID ANALOGS

This is a division of a prior application, Ser. No. 769,268, filed Oct. 1, 1991, now U.S. Pat. No. 5,153,193.

The present invention relates to compounds having Formula I depicted below,

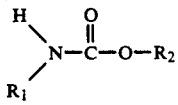
(I)

where
$R_1$ is

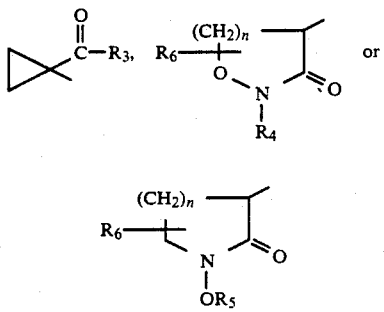 or

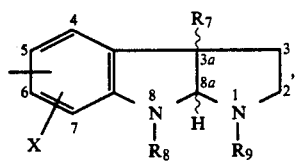

wherein
n is 1 or 2;
$R_3$ is hydroxy, loweralkoxy, arylloweralkoxy, amino, loweralkylamino or diloweralkylamino;
$R_4$ is hydrogen, loweralkyl or arylloweralkyl;
$R_5$ is hydrogen, loweralkyl, arylloweralkyl or loweralkylcarbonyl; and
$R_6$ is hydrogen or loweralkyl with the proviso that when $R_6$ is a loweralkyl group, it replaces one of the methylenic hydrogen atoms; and
$R_2$ is

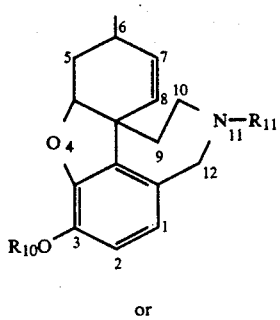

or

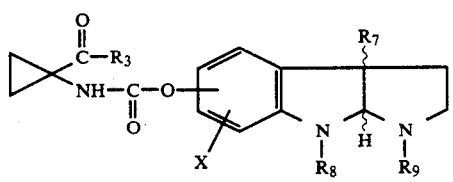

wherein
X is hydrogen, halogen, loweralkyl or loweralkoxy;
$R_7$ is loweralkyl or arylloweralkyl;
$R_8$ is hydrogen or loweralkyl;
$R_9$ is hydrogen, loweralkyl, loweralkenyl, loweralkynyl, arylloweralkyl, formyl, loweralkylcarbonyl, arylloweralkylcarbonyl or loweralkoxycarbonyl;
$R_{10}$ is hydrogen, loweralkyl, arylloweralkyl or loweralkylcarbonyl; and
$R_{11}$ is hydrogen, loweralkyl or arylloweralkyl; which compounds are useful for alleviating various memory dysfunctions characterized by a cholinergic deficit such as Alzheimer's disease.

Compounds of Formula I of this invention subsume compounds having Formulas II through VII depicted below.

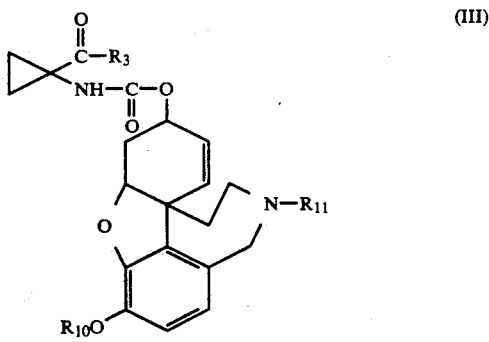
(II)

(III)

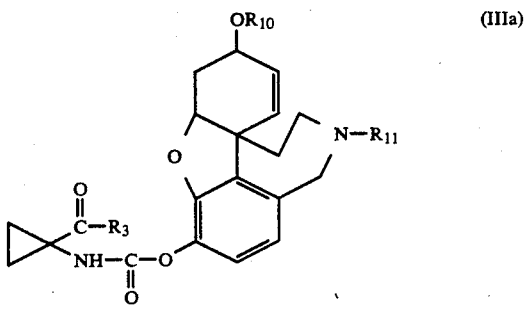
(IIIa)

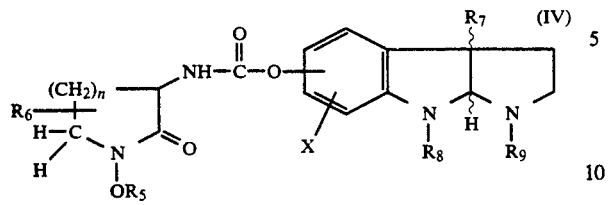

(IV)

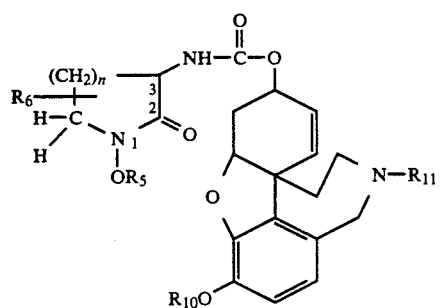

(V)

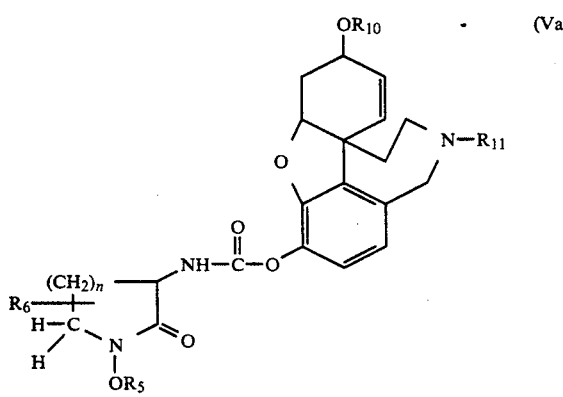

(Va)

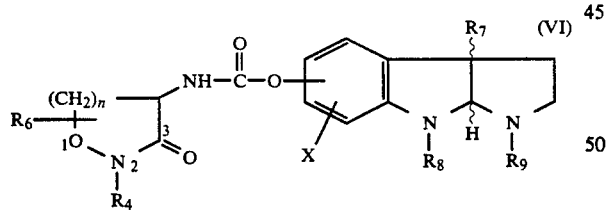

(VI)

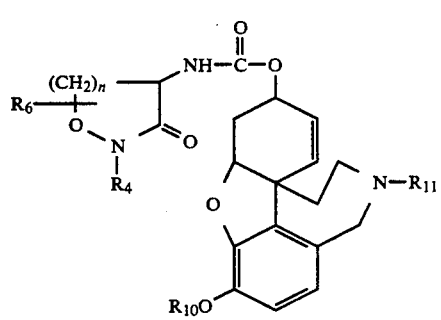

(VII)

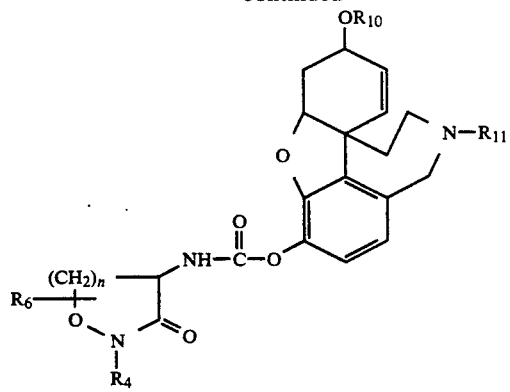

(VIIa)

Unless otherwise stated or indicated, the following definitions shall apply throughout the specification and the appended claims.

The term loweralkyl shall mean a straight or branched alkyl group having from 1 to 6 carbon atoms. Examples of said loweralkyl include methyl, ethyl, n-propyl, isopropyl, iso-butyl, sec-butyl and straight- and branched-chain pentyl and hexyl.

The term aryl shall mean a phenyl group optionally substituted with 1,2 or 3 substituents each of which being independently loweralkyl, loweralkoxy, hydroxy, halogen, trifluoromethyl or nitro.

The term halogen shall mean fluorine, chlorine, bromine or iodine.

Throughout the specification and the appended claims, a given chemical formula or name shall encompass all geometric, stereo, optical and tautomeric isomers where such isomers exist.

The compounds of this invention are prepared by utilizing one or more of the synthetic steps described below.

Throughout the description of the synthetic steps, the notations n, X and $R_1$ through $R_{11}$ shall have the respective meanings given above unless otherwise stated or indicated.

STEP A

A compound of Formula VIII (see for instance, Hamer et al., U.S. Pat. No. 4,791,107 as to the synthesis thereof) is hydrolyzed in situ and coupled with a compound of Formula IX, where $R_1$ is as defined earlier except that neither the parameter $R_4$ nor $R_5$ (used for defining $R_1$ and constituting a part thereof) may be hydrogen, to afford a compound of Formula X.

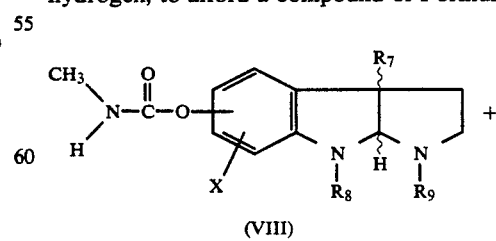

(VIII)

$R_1NH_2 \longrightarrow$ (IX)

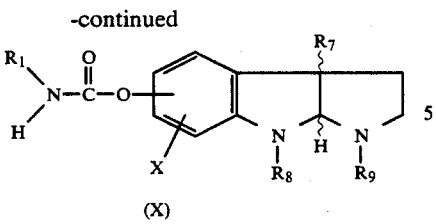

(X)

This reaction is typically conducted by first allowing compound VIII to react with a strong base such as potassium tertiary butoxide at a temperature of about 0° to 25° C. and thereafter adding carbonyldiimidazole and compound IX to the reaction mixture and stirring the resultant mixture at a temperature of about −30° to +25° C.

As to the preparation of the starting compounds of Formula IX where $R_1$ is

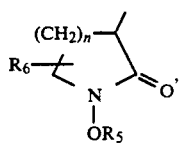

the reader is referred, for instance, to European Patent Application 0,318,091 (1989). As to the preparation of the starting compounds of Formula IX, where $R_1$ is

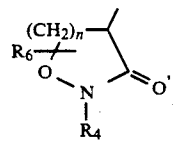

the reader is referred to J. Med. Chem., 13, 1013 (1970).

STEP B

Galanthamine or a substituted galanthamine analog depicted by Formula XI is allowed to react with carbonyldiimidazole in a suitable solvent such as tetrahydrofuran at a temperature of about 0° to 30° C. and thereafter, the resultant reaction intermediate is allowed to react with compound IX in the presence of acetic acid at a temperature of about 0° to 40° C. to afford a compound of Formula XII.

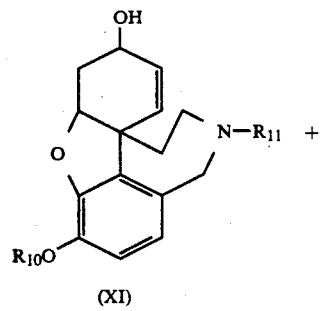

(XI)

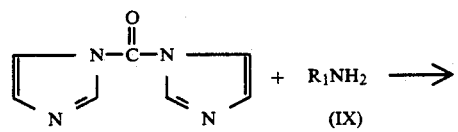

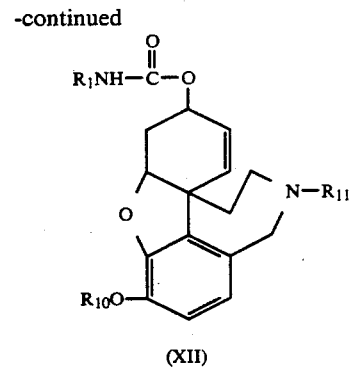

(XII)

Galanthamine is a natural product isolated from amaryllidaceae (caucasian snowdrops) and presently commercially available. As to the total synthesis of galanthamine, the reader is referred, for instance, to Barton and Kirby, J. Chem. Soc., 1962, 806; Koga, Heterocycles, 8, 277 (1977); and Szewczyk et al., J. Heterocyclic Chem., 25, 1809 (1988).

Similarly to the above, a compound of Formula XIII is allowed to react with carbonyldiimidazole and the resultant reaction intermediate is allowed to react with compound IX in substantially the same manner as described above to afford a compound of Formula XIV.

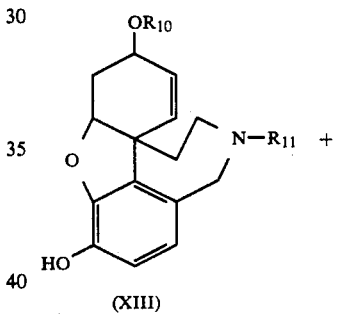

(XIII)

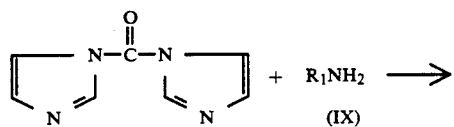

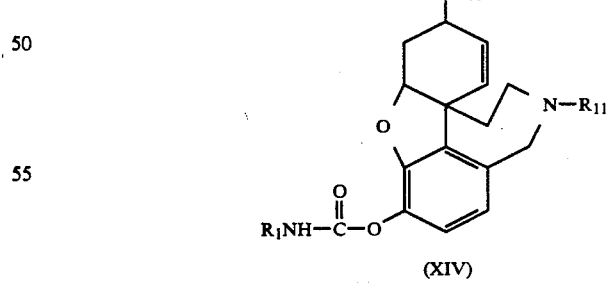

(XIV)

STEP C

A compound of Formula XV obtained from STEP A or B is allowed to react with 1,4-cyclohexadiene in the presence of palladium on carbon to afford a compound of Formula XVI (hydrogen transfer reaction, See Felix et al., J. Org. Chem., 43, 4194 (1978)). This reaction is typically conducted in the presence of a suitable solvent such as absolute ethanol at a temperature of about 0° to 25°.

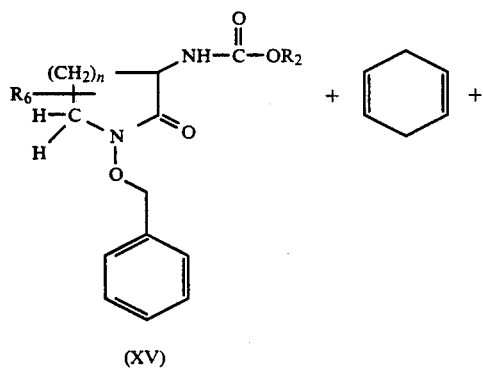

(XV)

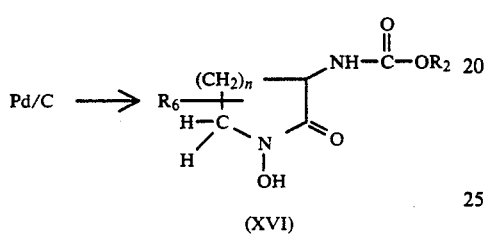

(XVI)

STEP D

A compound of Formula XVII obtained from STEP A or B is subjected to a hydrogenation reaction conducted in a routine manner known to the art to afford a compound of Formula XVIII.

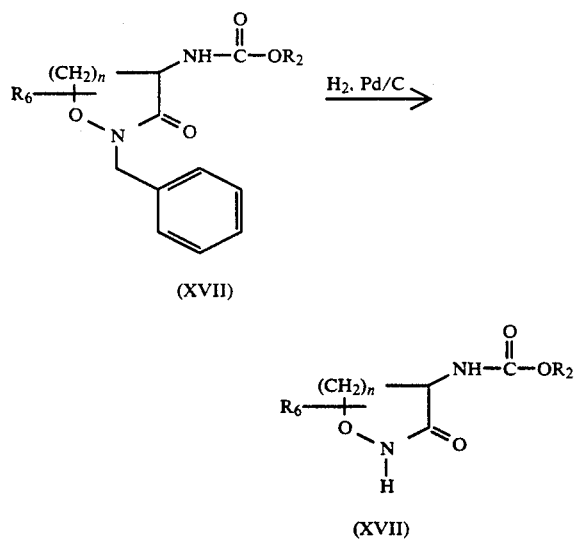

The compounds of Formula I of the present invention are useful for the treatment of various memory dysfunctions characterized by a cholinergic deficit such as Alzheimer's disease.

The activity to alleviate such memory dysfunctions is manifested by the ability of these compounds to inhibit the enzyme acetylcholinesterase and thereby increase acetylcholine levels in the brain.

Cholinesterase Inhibition Assay

Cholinesterases are found throughout the body, both in the brain and in serum. However, only brain acetylcholinesterase (AChE) distribution is correlated with central cholinergic innervation. This same innervation is suggested to be weakened in Alzheimer patients. We have determined in vitro inhibition of acetylcholinesterase activity in rat striatum.

In Vitro Inhibition of Acetylcholinesterase Activity in Rat Striatum

Acetylchlinesterase (AChE), which is sometimes called true or specific cholinesterase, is found in nerve cells, skeletal muscle, smooth muscle, various glands and red blood cells. AChE may be distinguished from other cholinesterases by substrate and inhibitor specificities and by regional distribution. Its distribution in brain roughly correlates with cholinergic innervation and subfractionation shows the highest level in nerve terminals.

It is generally accepted that the physiological role of AChE is the rapid hydrolysis and inactivation of acetylcholine. Inhibitors of AChE show marked cholinomimetic effects in cholinergically-innervated effector organs and have been used therapeutically in the treatment of glaucoma, myasthenia gravis and paralytic ileus. However, recent studies have suggested that AChE inhibitors may also be beneficial in the treatment of Alzheimer's disease.

The method described below was used in this invention for assaying cholinesterase activity. This is a modification of the method of Ellman et al., Biochem. Pharmacol. 7, 88 (1961).

Procedure

A. Reagents
  1. 0.05M Phosphate buffer, pH 7.2
     (a) 6.85 g $NaH_2PO_4.H_2O$/100 ml distilled $H_2O$
     (b) 13.40 g $Na_2HPO_4.7H_2O$/100 ml distilled $H_2O$
     (c) add (a) to (b) until pH reaches 7.2
     (d) Dilute 1:10
  2. Substrate in buffer
     (a) 198 mg acetylthiocholine chloride (10 mM)
     (b) bring to 100 ml with 0.05M phosphate buffer, pH 7.2 (reagent 1)
  3. DTNB in buffer
     (a) 19.8 mg 5,5-dithiobisnitrobenzoic acid (DTNB) (0.5 mM)
     (b) bring to 100 ml with 0.05M phosphate buffer, pH 7.2 (reagent 1)
  4. A 2 mM stock solution test drug is made up in a suitable solvent and brought to volume with 0.5 mM DTNB (reagent 3). Drugs are serially diluted (1:10) such that the final concentration (in cuvette) is $10^{-4}M$ and screened for activity. If active, $IC_{50}$ values are determined from the inhibitory activity of subsequent concentrations.

B. Tissue Preparation
  Male Wistar rats are decapitated, brains rapidly removed, corpora striata dissected free, weighed and homogenized in 19 volumes (approximately 7 mg protein/ml) of 0.05M phosphate buffer, pH 7.2 using a Potter-Elvehjem homogenizer. A 25 microliter aliquot of the homogenate is added to 1.0 milliter vehicle or various concentrations of the test drug and preincubated for 10 minutes at 37° C.

C. Assay
  Enzyme activity is measured with the Beckman DU-50 spectrophotometer. This method can be used for $IC_{50}$ determinations and for measuring kinetic constants.

Instrument Settings
  Kinetics Soft-Pac Module #598273 (10)
  Program #6 Kindata:
  Source—Vis
  Wavelength—412 nm
  Sipper-none
  Cuvettes—2 ml cuvettes using auto 6-sampler
  Blank—1 for each substrate concentration
  Interval time—15 seconds (15 or 30 seconds for kinetics)
  Total time—5 minutes (5 or 10 minutes for kinetics)
  Plot—yes
  Span—autoscale
  Slope—increasing
  Results—yes (gives slope)
  Factor—1
  Reagents are added to the blank and sample cuvettes as follows:
Blank:
  0.8 ml Phosphate Buffer/DTNB
  0.8 ml Buffer/Substrate
Control:
  0.8 ml Phosphate Buffer/DTNB/Enzyme
  0.8 ml Phosphate Buffer/Substrate
Drug:
  0.8 ml Phosphate Buffer/DTNB/Drug/Enzyme
  0.8 ml Phosphate Buffer/Substrate Blank values are determined for each run to control for non-enzymatic hydrolysis of substrate and these values are automatically subtracted by the kindata program available on kinetics soft-pac module. This program also calculates the rate of absorbance change for each cuvette.

For IC$_{50}$ Determinations

Substrate concentration is 10 mM diluted 1:2 in assay yielding final concentration of 5 mM. DTNB concentration is 0.5 mM yielding 0.25 mM final concentration.

$$\% \text{ Inhibition} = \frac{\text{slope control} - \text{slope drug}}{\text{slope control}} \times 100$$

IC$_{50}$ values are calculated from log-probit analysis

Results of this assay for some of the compounds of this invention and physostigmine (reference compound) are presented in Table 1.

TABLE 1

| Compound | IC$_{50}$(μM) |
|---|---|
| (3aS-cis)-1,2,3,3a,8,8a-Hexahydro-1,3a,8-trimethylpyrrolo[2,3-b]indol-5-yl[2-oxo-1-(phenylmethoxy)-3R-pyrrolidinyl]carbamate | 0.067 |
| (3aS-cis)-1,2,3,3a,8,8a-Hexahydro-1,3a,8-trimethylpyrrolo[2,3-b]indol-5-yl[2-(phenylmethyl)-3-oxo-4R-isoxazolidinyl]carbamate hemihydrate | 0.50 |
| (3aS-cis)-1,2,3,3a,8,8a-Hexahydro-1,3a,8-trimethylpyrrolo[2,3-b]indol-5-yl[2-oxo-1-(hydroxy)-3R-pyrrolidinyl]carbamate, citrate salt (Reference Compound) | 2.31 |
| Physostigmine | 0.034 |

This utility is further demonstrated by the ability of these compounds to restore cholinergically deficient memory in the Dark Avoidance Assay described below.

Dark Avoidance Assay

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic agent that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment.

Results of this assay for some of the compounds of this invention and those for tacrine (reference compound) are presented in Table 2.

TABLE 2

| Compound | Dose (mg/kg of body weight, s.c) | % of Animals with Scopolamine Induced Memory Deficit Reversal |
|---|---|---|
| (3aS-cis)-1,2,3,3a,8,8a-Hexahydro-1,3a,8-trimethyl-pyrrolo[2,3-b]indol-5-yl[2-(phenylmethyl)-3-oxo-4R-isoxazolidinyl]carbamate hemihydrate (Reference Compound) | 0.3 | 27 |
| Tacrine | 0.63 | 13 |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric, 2-naphthalenesulfonic and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweeting agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:

(3aS-cis)-1,2,3,3a,8,8a-hexahydro-1,3a,8-trimethylpyrrolo[2,3-b]indol-5-yl [2-(phenylmethyl)-3-oxo-4R-isoxazolidinyl]carbamate;

[4aS-(4aα,6β,8aR*)]-4a,5,9,10,11,12-hexahydro-3-methoxy-11-methyl-6H-benzofuro[3a,3,2-ef][2]benzazepin-6-yl [2-(phenylmethyl)-3-oxo-4R-isoxazolidinyl]carbamate;

[4aS-(4aα,6β,8aR*)]-4a,5,9,10,11,12-hexahydro-3-methoxy-11-methyl-6H-benzofuro[3a,3,2-ef][2]benzazepin-6-yl [2-oxo-1-(phenylmethoxy)-3R-pyrrolidinyl]carbamate;

(3aS-cis)-1,2,3,3a,8,8a-hexahydro-1,3a,8-trimethylpyrrolo[2,3-b]indol-5-yl [2-oxo-1-(phenylmethoxy)-3R-pyrrolidinyl]carbamate;

(3aS-cis)-1,2,3,3a,8,8a-hexahydro-1,3a,8-trimethylpyrrolo[2,3-b]indol-5-[2-oxo-1-(hydroxy)-3R-pyrrolidinyl]carbamate;

(3aS-cis)-[[[(1,2,3,3a,8,8a-hexahydro-1,3a,8-trimethylpyrrolo[2,3-b]indol-5-yl)oxy]carbonyl]amino]cyclopropanecarboxylic acid methyl ester;

(3aS-cis)-[[[(1,2,3,3a,8,8a-hexahydro-1,3a,8-trimethylpyrrolo[2,3-b]indol-5-yl)oxy]carbonyl]amino]cyclopropanecarboxylic acid methyl ester;

(3aS-cis)-[[[(1,2,3,3a,8,8a-hexahydro-1,3a,8-trimethylpyrrolo[2,3-b]indol-5-yl)oxy]carbonyl]amino]cyclopropanecarboxylic acid;

[4aS-(4aα,6β8aR*)]-1-[[[(4a,5,9,10,11,12-hexahydro-3-methoxy-11-methyl-6H-benzofuro[3a,3,2-ef][2]benzazepin-6-yl)oxy]carbonyl]amino]cyclopropanecarboxylic acid;

[4aS-(4aα,6β,8aR*)]-1-[[[(4a,5,9,10,11,12-hexahydro-3-methoxy-11-methyl-6H-benzofuro[3a,3,2-ef][2]benzazepin-6-yl)oxy]carbonyl]amino]cyclopropanecarboxylic acid methyl ester;

(3aS-cis)-1,2,3,3a,8,8a-hexahydro-1,3a,8-trimethylpyrrolo[2,3-b]indol-5-yl [2-(phenylmethyl)-3-oxo-4S-isoxazolidinyl]carbamate;

(3aS-cis)-1,2,3,3a,8,8a-hexahydro-1,3a,8-trimethylpyrrolo[2,3-b]indol-5-yl [2-oxo-1-(phenylmethoxy)-3s-pyrrolidinyl]carbamate;

(3aS-cis)-1,2,3,3a,8,8a-hexahydro-1,3a,8-trimethylpyrrolo[2,3-b]indol-5-yl [2-oxo-1-(hydroxy)-3S-pyrrolidinyl]carbamate;

(3aS-cis)-1,2,3,3a,8,8a-hexahydro-1,3a,8-trimethylpyrrolo[2,3-b]indol-5-yl [2-(phenylethyl)-3-oxo-4R-isoxazolidinyl]carbamate;

(3aS-cis)-1,2,3,3a,8,8a-hexahydro-1,3a,8-trimethylpyrrolo[2,3-b]indol-5-yl [2-oxo-1-(phenylethoxy)-3R-pyrrolidinyl]carbamate;

(3aS-cis)-1,2,3,3a,8,8a-hexahydro-1,3a,8-trimethylpyrrolo[2,3-b]indol-5-yl [2-(phenylethyl)-3-oxo-4S-isoxazolidinyl]carbamate;

(3aS-cis)-1,2,3,3a,8a-hexahydro-1,3a,8-trimethylpyrrolo[2,3-b]indol-5-yl [2-oxo-1-(phenylethoxy)-3S-pyrrolidinyl]carbamate;

(3aS-cis)-1,2,3,3a,8,8a-hexahydro-1,3a,8-trimethylpyrrolo[2,3-b]indol-5-yl [2-methyl-3-oxo-4R-isoxazolidinyl]carbamate;

(3aS-cis)-1,2,3,3a,8,8a-hexahydro-1,3a,8-trimethylpyrrolo[2,3-b]indol-5-yl [2-oxo-1-(methoxy)-3S-pyrrolidinyl]carbamate;

(3aS-cis)-1,2,3,3a,8,8a-hexahydro-1,3a,8-trimethylpyrrolo[2,3-b]indol-5-yl [2-oxo-1-methoxy)-3S-pyrrolidinyl]carbamate;

[4aS-(4aα,6β,8aR*)]-4a,5,9,10,11,12-hexahydro-6-hydroxy-11-methyl-6H-benzofuro[3a,3,2-ef][2]benzazepin-3-yl [2-oxo-1-(phenylmethoxy)-3R-pyrrolidinyl]carbamate;

[4aS-(4aα,6β,8aR*)]-4a,5,9,10,11,12-hexahydro-6-hydroxy-11-methyl-6H-benzofuro[3a,3,2-ef][2]benzazepin-3-yl [2-(phenylmethyl)-3-oxo-4R-isoxazolidinyl]carbamate;

[4aS-(4aα,6β,8aR*)]-4a,5,9,10,11,12-hexahydro-6-hydroxy-11-methyl-6H-benzofuro[3a,3,2-ef][2-ef]benzazepin-3-yl [2-oxo-1-(hydroxy)-3R-pyrrolidinyl]carbamate;

[4aS-(4aα,6β,8aR*)]-4a,5,9,10,11,12-hexahydro-6-hydroxy-11-methyl-6H-benzofuro[3a,3,2-ef][2]benzazepin-3-yl [3-oxo-(4R)-isoxazolidinyl]carbamate;

[4aS-(4aα,6β,8aR*)]-1-[[[(4a,5,9,10,11,12-hexahydro-6-hydroxy-11-methyl-6H-benzofuro[3a,3,2-ef][2]benzazepin-3-yl)oxy]carbonyl]amino]cyclopropanecarboxylic acid;

[4aS-(4aα,6β,8aR*)]-1-[[[(4a,5,9,10,11,12-hexahydro-6-hydroxy-11-methyl-6H-benzofuro[3a,3,2-ef][2]benzazepin-3-yl)oxy]carbonyl]-amino]cyclopropanecarboxylic acid methyl ester;

[4aS-(4aα,6β,8aR*)]-4a,5,9,10,11,12-hexahydro-6-hydroxy-11-methyl-6H-benzofuro[3a,3,2-ef][2]benzazepin-3-yl [1-[(diethylamino)carbonyl]cyclopropyl]carbamate;

[4aS-(4aα,6β,8aR*)-4a,5,9,10,11,12-hexahydro-3-methoxy-11-methyl-6H-benzofuro[3a,3,2-ef][2]benzazepin-6-yl [3-oxo-4R-isoxazolidinyl]carbamate;

(3aS-cis)-1,2,3,3a,8,8a-hexahydro-1,3a,8-trimethylpyrrolo-[2,3-b]indol-5-yl [3-oxo-4R-isoxazolidinyl]carbamate;

[4aS-(4aα,6β,8aR*)]-4a,5,9,10,11,12-hexahydro-3-methoxy-11-methyl-6H-benzofuro[3a,3,2-ef][2]benzazepin-6-yl [1-[(diethylamino)carbonyl]cyclopropyl]carbamate;

(3aS-cis)-1,2,3,3a,8,8a-hexahydro-1,3a,8-trimethylpyrrolo[2,3-b]indol-5-yl [1-[(diethylamino)carbonyl]cyclopropyl]carbamate;

[4aS-(4aα,6β,8aR*)]-4a,5,9,10,11,12-hexahydro-6-hydroxy-11-methyl-6H-benzofuro[3a,3,2-ef][2]benzazepin-3-yl [2-(methyl)-3-oxo-4R-isoxazolidinyl]carbamate;

[4aS-(4aα,6β,8aR*)]-4a,5,9,10,11,12-hexahydro-6-hydroxy-11-methyl-6H-benzofuro[3a,3,2-ef][2]benzazepin-3-yl [2-(methyl)-3-oxo-4S-isoxazolidinyl]carbamate;

[4aS-(4aα,6β,8aR*)]-4a,5,9,10,11,12-hexahydro-6-hydroxy-11-methyl-6H-benzofuro[3a,3,2-ef][2]benzazepin-3-yl) [2-oxo-1(phenylmethoxy)-3S-pyrrolidinyl]carbamate;

[4aS-(4aα,6β,8aR*)]-4a,5,9,10,11,12-hexahydro-3-methoxy-11-methyl-6H-benzofuro[3a,3,2-ef][2]benzazepin-6-yl [2-(methyl)-3-oxo-4S-isoxazolidinyl]carbamate;

[4aS-(4aα,6β,8aR*)]-4a,5,9,10,11,12-hexahydro-6-hydroxy-11-methyl-6H-benzofuro[3a,3,2-ef][2]benzazepin-3-yl [2-oxo-1-(methoxy)-3R-pyrrolidinyl]carbamate;

[4aS-(4aα,6β,8aR*)]-4a,5,9,10,11,12-hexahydro-3-methoxy-11-methyl-6H-benzofuro[3a,3,2-ef][2]benzazepin-6-yl [2-oxo-1-(methoxy)-3S-pyrrolidinyl]carbamate;

[4aS-(4aα,6β,8aR*)]-4a,5,9,10,11,12-hexahydro-6-hydroxy-11-methyl-6H-benzofuro[3a,3,2-ef][2]benzazepin-3-yl [3-oxo-4S-isoxazolidinyl]carbamate;

[4aS-(4aα,6β,8aR*)]-4a,5,9,10,11,12-hexahydro-3-methoxy-11-methyl-6H-benzofuro[3a,3,2-ef][2]benzazepin-6-yl [3-oxo-4S-isoxazolidinyl]carbamate;

(3aS-cis)-1,2,3,3a,8,8a-hexahydro-1,3a,8-trimethylpyrrolo[2,3-b]indol-5-yl [3-oxo-4S-isoxazolidinyl]carbamate;

(3aS-cis)-1,2,3,3a,8,8a-hexahydro-1,3a,8-trimethylpyrrolo[2,3-b]indol-5-yl [2-oxo-1-(hydroxy)-4-methyl-3-pyrrolidinyl]carbamate;

(3aS-cis)-1,2,3,3a,8,8a-hexahydro-1,3a,8-trimethylpyrrolo[2,3-b]indol-5-yl [2-oxo-1-(phenylmethoxy)-4-methyl-3-pyrrolidinyl]carbamate;

(3aS-cis)-1,2,3,3a,8,8a-hexahydro-1,3a,8-trimethylpyrrolo[2,3-b]indol-5-yl [2-oxo-1-(hydroxy)-5-methyl-3-pyrrolidinyl]carbamate;

(3aS-cis)-1,2,3,3a,8,8a-hexahydro-1,3a,8-trimethylpyrrolo[2,3-b]indol-5-yl [2-oxo-1-(phenylmethoxy)-5-methyl-3-pyrrolidinyl]carbamate;

[4aS-(4aα,6β,8aR*)]-4a,5,9,10,11,12-hexahydro-6-hydroxy-11-methyl-6H-benzofuro[3a,3,2-ef][2]benzazepin-3-yl [2-oxo-1-(hydroxy)-4-methyl-3-pyrrolidinyl]carbamate;

[4aS-(4aα,6β,8aR*)]-4a,5,9,10,11,12-hexahydro-6-hydroxy-11-methyl-6H-benzofuro[3a,3,2-ef][2]benzazepin-3-yl [2-oxo-1-(phenylmethoxy)-4-methyl-3-pyrrolidinyl]carbamate;

[4aS-(4aα,6β,8aR*)]-4a,5,9,10,11,12-hexahydro-6-hydroxy-11-methyl-6H-benzofuro[3a,3,2-ef][2]benzazepin-3-yl [2-oxo-1-(hydroxy)-5-methyl-3-pyrrolidinyl]carbamate;

[4aS-(4aα,6β,8aR*)]-4a, 5,9,10,11,12-hexahydro-6-hydroxy-11-methyl-6H-benzofuro[3a,3,2-ef][2]benzazepin-3-yl [2-oxo-1-(phenylmethoxy)-5-methyl-3-pyrrolidinyl]carbamate;

[4aS-(4aα,6β,8aR*)]-4a,5,9,10, 11,12-hexahydro-3-methoxy-11-methyl-6H-benzofuro]3a,3,2-ef][2]benzazepin-6-yl [2-oxo-1-(hydroxy)-4-methyl-3-pyrrolidinyl]carbamate;

[4aS-(4aα,6β,8aR*)]-4a,5,9,10, 11,12-hexahydro-3-methoxy-11-methyl-6H-benzofuro[3a,3,2-ef][2]benzazepin-6-yl [2-oxo-1-(phenylmethoxy)-4-methyl-3-pyrrolidinyl]carbamate;

[4aS-(4aα,6β,8aR*)]-4a,5,9,10, 11,12-hexahydro-3-methoxy-11-methyl-6H-benzofuro[3a,3,2-ef][2]benzazepin-6-yl [2-oxo-1-(hydroxy)-5-methyl-3-pyrrolidinyl]carbamate;

[4aS-(4aα,6β,8aR*)]-4a,5,9,10, 11,12-hexahydro-3-methoxy-11-methyl-6H-benzofuro[3a3,2-ef][2]benzazepin-6-yl [2-oxo-1-(phenylmethoxy)-5-methyl-3-pyrrolidinyl]carbamate;

[4aS-(4a,α,6β,8aR*)]-4a,5,9,10, 11,12-hexahydro-3-methoxy-11-methyl-6H-benzofuro[3a3,2-ef][2]benzazepin-6-yl [2-oxo-1-(phenylmethoxy)-3S-pyrrolidinyl]carbamate;

[4aS-(4aα,6β,8aR*)]-4a,5,9,10, 11,12-hexahydro-3-methoxy-11-methyl-6H-benzofuro[3a3,2-ef][2]benzazepin-6-yl [2-oxo-1-(hydroxy)-3R-pyrrolidinyl]carbamate;

[4aS-(4aα,6β,8aR*)]-4a,5,9,10,11, 12-hexahydro-3-methoxy-11-methyl-6H-benzofuro[3a,3,2-ef][2]benzazepin-6-yl [2-oxo-1-(hydroxy)-3S-pyrrolidinyl]carbomate;

[4aS-(4aα,6β,8aR*)]-4a,5,9,10,11, 12-hexahydro-3-methoxy-11-methyl-6H-benzofuro[3a,3,2-ef][2]benzazepin-6-yl [2-oxo-1-(phenylethoxy)-3R-pyrrolidinyl]carbamate;

[4aS-(4aα,6β,8aR*)]-4a,5,9,10,11, 12-hexahydro-6-hydroxy-11-methyl-6H-benzofuro[3a, 3,2-ef][2]benzazepin-3-yl [2-oxo-1-(hydroxy)-3S-pyrrolidinyl]carbamate;

[4aS-(4aα,6β,8aR*)]-4a,5,9,10,11,12-hexahydro-6-hydroxy-11-methyl-6H-benzofuro[3a,3,2-ef][2]benzazepin-3-yl [2-oxo-1-(phenylethoxy)-3R-pyrrolidinyl]carbamate;

[4aS-(4aα,6β,8aR*)]-4a,5,9,10,11,12-hexahydro-6-hydroxy-11-methyl-6H-benzofuro[3a,3,2-ef][2]benzazepin-3-yl [2-oxo-1-(phenylethoxy)-3S-pyrrolidinyl]carbamate;

[4aS-(4aα,6β,8aR*)]-4a,5,9,10,11,12-hexahydro-3-methoxy-11-methyl-6H-benzofuro[3a,3,2-ef][2]benzazepin-6-yl [2-(phenylethyl)-3-oxo-4S-isoxazolidinyl]carbamate;

[4aS-(4aα,6β,8aR*)]-4a,5,9,10,11,12-hexahydro-3-methoxy-11-methyl-6H-benzofuro[3a,3,2-ef][2]benzazepin-6-yl [2-(phenylethyl)-3-oxo-4R-isoxazolidinyl]carbamate;

[4aS-(4aα,6β,8aR*)]-4a,5,9,10,11,12-hexahydro-3-methoxy-11-methyl-6H-benzofuro[3a,3,2-ef][2]benzazepin-6-yl [2-(phenylmethyl)-3-oxo-4S-isoxazolidinyl]carbamate;

[4aS-(4aα,6β,8aR*)]-4a,5,9,10,11,12-hexahydro-3-methoxy-11-methyl-6H-benzofuro[3a,3,2-ef][2]benzazepin-6-yl [2-methyl-3-oxo-4R-isoxazolidinyl]carbamate;

[4aS-(4aα,6β,8aR*)]-4a,5,9,10,11,12-hexahydro-6-hydroxy-11-methyl-6H-benzofuro[3a,3,2-ef][2]benzazepin-3-yl [2-(phenylmethyl)-3-oxo-4S-isoxazolidinyl]carbamate;

[4aS-(4aα,6β,8aR*)]-4a,5,9,10,11,12-hexahydro-6-hydroxy-11-methyl-6H-benzofuro[3a,3,2-ef][2]benzazepin-3-yl [2-(phenylethyl)-3-oxo-4R-isoxazolidinyl]carbamate;

[4aS-(4aα,6β,8aR*)]-4a,5,9,10,11,12-hexahydro-6-hydroxy-11-methyl-6H-benzofuro[3a,3,2-ef][2]benzazepin-3-yl [2-(phenylethyl)-3-oxo-4S-isoxazolidinyl]carbamate;

(3aS-cis)-1,2,3,3a,8,8a-hexahydro-1,3a,8-trimethylpyrrolo[2,3-b]indol-5-yl [2-oxo-1-(phenylethoxy)-4-methyl-3-pyrrolidinyl]carbamate;

(3aS-cis)-1,2,3,3a,8,8a-hexahydro-1,3a,8-trimethylpyrrolo[2,3-b]-indol-5-yl [2-oxo-1-(methoxy)-4-methyl-3-pyrrolidinyl]carbamate;

(3aS-cis)-1,2,3,3a,8,8a-hexahydro-1,3a,8-trimethylpyrrolo[2,3-b]-indol-5-yl [2-oxo-1-(methoxy)-5-methyl-3-pyrrolidinyl]carbamate;

(3aS-cis)-1,2,3,3a,8,8a-hexahydro-1,3a,8-trimethylpyrrolo[2,3-b]-indol-5-yl [2-oxo-1-(phenylethoxy)-5-methyl-3-pyrrolidinyl]carbamate;

[4aS-(4aα,6β,8aR*)]-4a,5,9,10,11,12-hexahydro-3-methoxy-11-methyl-6H-benzofuro[3a,3,2-ef][2]benzazepin-6-yl [2-oxo-1-(phenylethoxy)-5-methyl-3-pyrrolidinyl]carbamate;

[4aS-(4aα,6β,8aR*)]-4a,5,9,10,11,12-hexahydro-3-methoxy-11-methyl-6H-benzofuro[3a,3,2-ef][2]benzazepin-6-yl [2-oxo-1-(methoxy)-5-methyl-3-pyrrolidinyl]carbamate;

[4aS-(4aα,6β,8aR*)]-4a,5,9,10,11,12-hexahydro-3-methoxy-11-methyl-6H-benzofuro[3a,3,2-ef][2]benzazepin-6-yl [2-oxo-1-(methoxy)-4-methyl-3-pyrrolidinyl]]carbamate;

[4aS-(4aα,6β,8aR*)]-4a,5,9,10,11,12-hexahydro-6-hydroxy-11-methyl-6H-benzofuro[3a,3,2-ef][2]benzazepin-3-yl [2-oxo-1-(methoxy)-4-methyl-3-pyrrolidinyl]carbamate;

[4aS-(4aα,6β,8aR*)]-4a,5,9,10,11,12-hexahydro-6-hydroxy-11-methyl-6H-benzofuro[3a,3,2-ef][2]benzazepin-3-yl [2-oxo-1-(phenylethoxy)-5-methyl-3-pyrrolidinyl]carbamate;

[4aS-(4aα,6β,8aR*)]-4a,5,9,10,11,12-hexahydro-6-hydroxy-11-methyl-6H-benzofuro[3a,3,2-ef][2]benzazepin-3yl [2-oxo-1-(methoxy)-5-methyl-3-pyrrolidinyl]carbamate;

[4aS-(4aα,6β,8aR*)]-4a,5,9,10,11,12-hexahydro-3-methoxy-11-methyl-6H-benzofuro[3a,3,2-ef][2]benzazepin-6-yl [2-oxo-1-(methoxy)-3R-pyrrolidinyl]carbamate;

[4aS-(4aα,6β,8aR*)]-4a,5,9,10,11,12-hexahydro-6-hydroxy-11-methyl-6H-benzofuro[3a,3,2-ef][2]benzazepin-3-yl [2-oxo-1-(phenylethoxy)-3S-pyrrolidinyl]carbamate;

[4aS-(4aα,6β,8aR*)]-4a,5,9,10,11,12-hexahydro-6-hydroxy-11-methyl-6H-benzofuro[3a,3,2-ef][2]benzazepin-3-yl [2-oxo-1-(methoxy)-3S-pyrrolidinyl]carbamate; and (3aS-cis)-1,2,3,3a,8,8a-hexahydro-1,3a,8-trimethylpyrrolo[2,3-b]indol-5-yl [2-(methyl)-3-oxo-4S-isoxazolidinyl]carbamate;

The following examples are presented in order to illustrate the present invention.

EXAMPLE 1

(3aS-cis)-1,2,3,3a,8,8a-Hexahydro-1,3a,8-trimethypyrrolo-[2,3-b]indol-5-yl
[2-(phenylmethyl)-3-oxo-4R-isoxazolidinyl]-carbamate hemihydrate To a reaction system completely free of air and moisture was added physostigmine as the free base (0.55 g) and degassed, anhydrous tetrahydrofuran (THF, 5 ml). The mixture was cooled to 0° C., treated with potassium tert-butoxide (0.22 g) and stirred at this temperature for 20 minutes. The temperature was lowered to −30° C., and the mixture was treated with glacial acetic acid (0.10 ml) and carbonyldiimidazole (0.26 g), and held at −30° C. for four hours. A solution prepared from 4-amino-2-(phenylmethyl)-3-isoxazolidinone (0.38 g) in THF (2 ml) and glacial acetic acid (0.56 ml) was then added, and the stirred mixture allowed to warm to room temperature overnight. The THF was removed on a rotary evaporator and the residue taken up in ethyl acetate (100 ml.) The mixture was washed successively with brine (2×50 ml), saturated NaHCO$_3$ (2×50 ml) and brine (1×50 ml.) The organic extracts were dried (Na$_2$SO$_4$), filtered and concentrated to a dark amber which was purified by preparative HPLC (silica gel) with 5% methanol in dichloromethane as the loading solvent and eluent. The appropriate fractions were combined and concentrated to a yellow foam (0.40 g) which was pure by TLC (silica gel).

| Analysis: | | | |
|---|---|---|---|
| Calculated for C$_{24}$H$_{28}$N$_4$O$_4$·½H$_2$O: | 64.64% C; | 6.56% H; | 12.58% N |
| Found: | 64.94% C; | 6.47% H; | 12.94% N |

EXAMPLE 2

(3aS-cis)-1,2,3,3a,8,8a-Hexahydro-1,3a,8-trimethylpyrrolo-[2,3-b]indol-5yl
[2-oxo-1-(phenylmethoxy)-3R-pyrrolidinyl]carbamate A 50 ml three-neck round bottom flask was evacuated and flushed with N$_2$ to completely exclude air and moisture. Physostigmine (0.64 g) was added followed by anhydrous THF (7 ml, freshly degassed). The solution was cooled to −5° C. and treated with potassium tert-butoxide (0.287 g) via gooche tube addition. The mixture became bright yellow and was stirred at this temperature for 15 minutes under N$_2$. The temperature was lowered to −30° C. (dry ice/MeOH bath) and acetic acid (0.13 ml) was added, followed by dry carbonyldiimidazole (0.27 g). The solution became light red to brown in color and was held at this temperature for 3.5 hours. A solution of (3R)-3-amino-1-phenylmethoxypyrrolidin-2-one (0.48 g) in the THF (2 ml) was added via canula along with acetic acid (0.70 ml). The mixture was allowed to gradually warm to room temperature and stirred overnight. The mixture was then cooled with an ice bath and neutralized with saturated aqueous sodium bicarbonate solution. The THF was removed on a rotary evaporator and the residue dissolved in EtOAc. The mixture was extracted twice with brine, dried (Na₂SO₄), filtered and concentrated to an amber oil. The material was purified via preparative HPLC (silica gel column) with 5% methanol in DCM used as loading solvent and eluant. The appropriate fractions were combined and concentrated to afford 0.27 g of a foam, which was triturated with diethyl ether and hexane to afford a low melting solid, mp 55°-65° C.

| | Analysis: | | |
|---|---|---|---|
| Calculated for C₂₅H₃₀N₄O₄: | 66.65% C | 6.71% H | 12.44% N |
| Found: | 66.03% C | 6.71% H | 12.28% N |

EXAMPLE 3

(3aS-cis)-1,2,3,3a,8,8a-Hexahydro-1,3a,8-trimethylpyrrolo[2,3-b]indol-5-yl [2-oxo-1-(hydroxy)-3R-pyrrolidinyl]carbamate, citrate salt To a solution of (3aS-cis)-1,2,3,3a,8,8a-hexahydro-1,3a,8-trimethylpyrrolo[2,3-b]indol-5-yl [2-oxo-1-(phenylmethoxy)-3R-pyrrolidinyl]carbamate (0.26 g) in absolute ethanol (6 ml) was added 10% palladium on activated carbon (0.24 g) under a nitrogen atmosphere with stirring. 1,4-Cyclohexadiene (0.90 ml) was added at room temperature and the solution was stirred for 12 hours. Product formation was detected by TLC using a 2% FeCl₃(ethanol) stain. The mixture was filtered through Celite ® and washed repeatedly with ethanol followed by dichloromethane. The filtrate was concentrated under reduced pressure and purified via flash column chromatography (silica gel) using 30% methanol in DCM as eluent to afford a tan solid (0.15 g). The material was suspended in dry diethyl ether, and methanol was added dropwise until all material had gone into solution. One equivalent of a 0.1M solution of citric acid in diethyl ether was added. The salt which precipitated was filtered, and dried under reduced pressure over toluene, m.p. 133° C.-153° C. The material was pure by TLC.

| | Analysis: | | |
|---|---|---|---|
| Calculated for C₂₄H₃₂N₄O₁₁: | 52.17% C | 5.84% H | 10.14% N |
| Found: | 52.05% C | 5.98% H | 10.19% N |

EXAMPLE 4

[4aS-(4aα,6β,8aR*)]-4a,5,9,10,11,12-hexahydro-3-methoxy-11-methyl-6H-benzofuro[3a,3,2-ef][2]benzazepine-6-yl [2-(phenylmethyl)-3-oxo-4R-isoxazolidinyl]carbamate A three-neck round bottom flask equipped with a gooche tube, rubber septum and N₂ inlet was charged with galanthamine (0.30 g), evacuated and purged with N₂ to remove all traces of air and moisture. The solid was dissolved in anhydrous, degassed THF (9 ml) and treated with carbonyldiimidazole (0.20 g). The mixture was stirred for 12 hours at room temperature, cooled to 0° C. and treated with glacial acetic acid (0.20 ml) followed by a solution of 4-amino-2-phenylmethyl-3-isoxazolidinone (0.24 g) in THF (2 ml). The mixture was stirred for 12 hours, cooled to 0° C. and neutralized with a saturated aqueous NaHCO₃ solution. The solvent was removed under reduced pressure, dissolved in ethyl acetate and washed successively with saturated aqueous NaHCO₃ (1×100 ml), and brine (1×100 ml), and dried (Na₂SO₄). The mixture was filtered and concentrated to an amber oil which was purified via HPLC (silica gel) using 5% MeOH in DCM as the loading solvent and eluant. The appropriate fractions were combined and concentrated yielding of tan solid. This material appeared pure by TLC and the mass spectrum (chemical ionization, MH+506) was consistent with the product.

EXAMPLE 5

[4aS-(4aα,6β,8aR*)]-4a,5,9,10,11,12-hexahydro-3-methoxy-11-methyl-6H-benzofuro[3a,3,2-ef][2]benzazepine-6-yl [2-oxo-1-(phenylmethoxy)-3R-pyrrolidinyl]carbamate A three-necked round bottom flask equipped with a gouche tube, rubber septum and N₂ inlet was evacuated and purged with nitrogen to remove all traces of air and moisture. The vessel was charged with galanthamine (0.39 g) and anhydrous, degassed THF (11.0 ml). After cooling to 0° C. with an ice bath, carbonyldiimidazole (0.26 g) was added via the gooche tube and the mixture was stirred at room temperature for 4 hours. The reaction mixture was then cooled to 0° C. and treated with glacial acetic acid (0.10 ml) followed by a solution of (3R)-3-amino-1-phenylmethoxypyrrolidin-2-one (0.33 g) in THF (4.0 ml). The mixture was stirred at room temperature under N₂ for 20 hours. The mixture was cooled to 0° C. and a saturated aqueous NaHCO₃ solution was added to obtain a pH of 7-8. The solvent was removed under reduced pressure and ethyl acetate was added. The organic phase was washed successively with saturated aqueous NaHCO₃ (2×100 ml), and brine (1×100 ml), and dried (Na₂SO₄). Filtration and solvent removal yielded an amber oil which was purified by HPLC (silica gel), loading and eluting with 5% methanol in DCM. The appropriate fractions were combined and concentrated to afford 400 mg of light yellow hygroscopic foam. This material appeared pure by TLC and the mass spectrum (chemical ionization, MH⊕520) was consistent with the product.

| | Analysis: | | |
|---|---|---|---|
| Calculated for C₂₉H₃₃N₃O₆: | 67.04% C | 6.04% H | 8.09% N |
| Found: | 66.42% C | 6.41% H | 8.40% N |

We claim:
1. A compound having the formula,

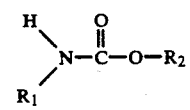

where
R₁ is

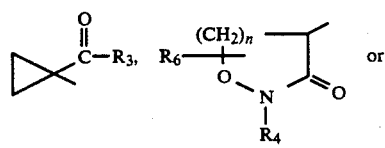

-continued

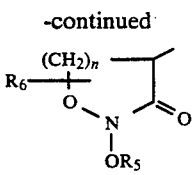

wherein
n is 1 or 2; $R_3$ is hydroxy, loweralkoxy, aryl-loweralkoxy, amino, loweralkylamino or diloweralkylamino; $R_4$ is hydrogen, loweralkyl or arylloweralkyl;

$R_5$ is hydrogen, loweralkyl, arylloweralkyl or loweralkylcarbonyl; and $R_6$ is hydrogen or loweralkyl with the proviso that when $R_6$ is a loweralkyl group, it replaced one of the methylenic hydrogen atoms; and $R_2$ is

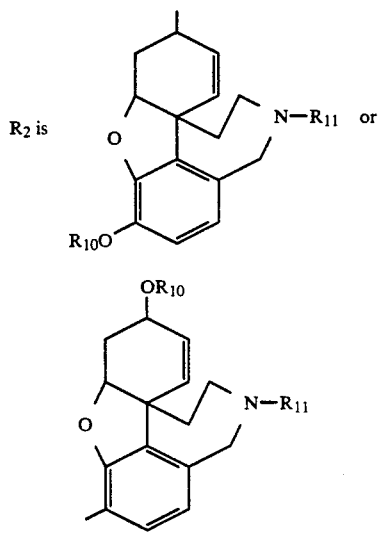

wherein
$R_{10}$ is hydrogen, loweralkyl, arylloweralkyl or loweralkylcarbonyl; and $R_{11}$ is hydrogen, loweralkyl or arylloweralkyl; or a pharmaceutically acceptable acid addition salt thereof.

2. The compound as defined in claim 1, which is [4aS-(4aα,6β,8aR*)]-4a,5,9,10,11,12-hexahydro-3-methoxy-11-methyl-6H-benzofuro-[3a,3,2-ef] [2]benzazepine-6-yl [2-(phenylmethyl)-3-oxo-4R-isoxazolidinyl]-carbamate.

3. The compound as defined in claim 1, which is [4aS-(4aα,6β,8aR*)]-4a,5,9,10,11,12-hexahydro-3-methoxy-11-methyl-6H-benzofuro-[3a,3,2-ef][2]benzazepine-6-yl [2-oxo-1-(phenylmethoxy)-3R-pyrrolidinyl]carbamate.

4. The compound as defined in claim 1, which is [4aS-(4aα,6β, 8aR*)]-4a,5,9,10,11,12-hexahydro-3-methoxy-11-methyl-6H-benzofuro[3a,3,2-ef][2]benzazepin-6-yl [2-(methyl)-3-oxo-4R-isoxazolidinyl]carbamate.

5. The compound as defined in claim 1, which is [4aS-(4aα,6β,8aR*)]-4a,5,9,10,11,12-hexahydro-3-methoxy-11-methyl-6H-benzofuro[3a,3,2-ef][2]benzazepin-6-yl [3-oxo-4R-isoxazolidinyl]carbamate;

6. The compound as defined in claim 1, which is [4aS-(4aα,6β,8aR*)]-4a,5,9,10,11,12-hexahydro-3-methoxy-11-methyl-6H-benzofuro[3a,3,2-ef][2]benzazepin-6-yl [2-oxo-1-(methoxy)-3R-pyrrolidinyl]carbamate.

7. The compound as defined in claim 1, which is [4aS-(4aα,6β,8aR*)]-4a,5,9,10,11,12-hexahydro-3-methoxy-11-methyl-6H-benzofuro[3a,3,2-ef][2]benzazepin-6-yl [2-oxo-1-(hydroxy)-3R-pyrrolidinyl]carbamate.

8. The compound as defined in claim 1, which is [4aS-(4aα,6β,8aR*)]-1-[[[(4a,5,9,10,11,12-hexahydro-3-methoxy-11-methyl-6H-benzofuro[3a,3,2-ef][2]benzazepin-6-yl)oxy]carbonyl]amino]cyclopropanecarboxylic acid methyl ester.

9. The compound as defined in claim 1, which is [4aS-(4aα,6β,8aR*)]-4a,5,9,10,11,12-hexahydro-3-methoxy-11-methyl-6H-benzofuro[3a,3,2-ef][2]benzazepin-6-yl[2-(methyl)-3-oxo-4S-isoxazolidinyl]carbamate.

10. The compound as defined in claim 1, which is [4aS-(4aα,6β,8aR*)]-4a,5,9,10,11,12-hexahydro-3-methoxy-11-methyl-6H-benzofuro[3a,3,2-ef][2]benzazepin-6-yl [3-oxo-4S-isoxazolidinyl]carbamate.

11. The compound as defined in claim 1, which is [4aS-(4aα,6β,8aR*)]-4a,5,9,10,11,12-hexahydro-3-methoxy-11-methyl-6H-benzofuro[3a,3,2-ef][2]benzazepin-6-yl [2-oxo-1-(methoxy)-3S-pyrrolidinyl]carbamate.

12. The compound as defined in claim 1, which is [4aS-(4aα,6β,8aR*)]-4a,5,9,10,11,12-hexahydro-3-methoxy-11-methyl-6H-benzofuro[3a,3,2-ef][2]benzazepin-6-yl[2-oxo-1-(hydroxy)-3S-pyrrolidinyl]carbamate.

13. A pharmaceutical composition comprising a compound as defined in claim 1 in an amount effective for alleviating memory dysfunction, and a suitable carrier therefor.

14. A method of alleviating memory dysfunction which comprises administering to a patient an effective amount of a compound as defined in claim 1.

* * * * *